US011690503B2

(12) United States Patent
Hedges et al.

(10) Patent No.: US 11,690,503 B2
(45) Date of Patent: Jul. 4, 2023

(54) ENDOSCOPIC INSTRUMENT

(71) Applicant: ARTHREX, INC., Naples, FL (US)

(72) Inventors: Benjamin Perry Hedges, Santa Barbara, CA (US); Andrew W. Melton, Santa Barbara, CA (US); Ryan Kellar, Naples, FL (US); Zachary Dominguez, Carpinteria, CA (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 17/374,328

(22) Filed: Jul. 13, 2021

(65) Prior Publication Data

US 2022/0047153 A1   Feb. 17, 2022

Related U.S. Application Data

(60) Provisional application No. 63/065,037, filed on Aug. 13, 2020.

(51) Int. Cl.
*A61B 1/04* (2006.01)
*A61B 1/00* (2006.01)
*A61B 1/06* (2006.01)

(52) U.S. Cl.
CPC .......... *A61B 1/04* (2013.01); *A61B 1/00009* (2013.01); *A61B 1/00016* (2013.01);
(Continued)

(58) Field of Classification Search
CPC .......... A61B 1/00016; A61B 1/00018; A61B 1/00029; A61B 1/00032; A61B 1/00034; A61B 1/00066; A61B 1/00068; A61B 1/00071; A61B 1/00103; A61B 1/00105; A61B 1/00108; A61B 1/0011; A61B 1/00114; A61B 1/00124; A61B 1/00195;
(Continued)

(56) References Cited

U.S. PATENT DOCUMENTS 5,653,677 A * 8/1997 Okada ................ A61B 1/053
600/113
6,319,195 B1 * 11/2001 Nakaichi .............. A61B 1/267
600/150
(Continued)

FOREIGN PATENT DOCUMENTS

EP      0726733      6/1999

OTHER PUBLICATIONS

International Search Report and Written Opinion for International Application No. PCT/US2021/041397 completed Oct. 12, 2021.
(Continued)

*Primary Examiner* — Aaron B Fairchild
*Assistant Examiner* — Stephen Floyd London
(74) *Attorney, Agent, or Firm* — Carlson, Gaskey & Olds, P.C.

(57) ABSTRACT

This disclosure relates to instruments and methods of performing an endoscopy. An endoscope for producing images of a surgery in vivo may include a hub and an imaging rod extending from the hub, the imaging rod being configured to receive light and direct the light to an imaging sensor located adjacent to a distal end of the imaging rod, the hub and the imaging rod being attached to form an assembly having a center of mass established distally of the hub. In other implementations, the hub may be omitted.

18 Claims, 8 Drawing Sheets

(52) U.S. Cl.
CPC ...... *A61B 1/00027* (2013.01); *A61B 1/00114* (2013.01); *A61B 1/00126* (2013.01); *A61B 1/0607* (2013.01)

(58) Field of Classification Search
CPC ....... A61B 1/00197; A61B 1/041; A61B 1/05; A61B 1/051; A61B 1/053; A61B 1/0669; A61B 5/0066; A61B 2017/291; A61M 25/0097; H01B 9/003; H02J 2310/23
See application file for complete search history.

(56) References Cited

U.S. PATENT DOCUMENTS

| | | | | |
|---|---|---|---|---|
| 2005/0182297 | A1* | 8/2005 | Gravenstein | A61B 1/042 |
| | | | | 600/139 |
| 2006/0212056 | A1* | 9/2006 | Salvadori | A61M 1/00 |
| | | | | 606/167 |
| 2007/0244354 | A1* | 10/2007 | Bayer | A61B 1/005 |
| | | | | 600/101 |
| 2009/0294150 | A1* | 12/2009 | McGinley | H02J 7/0042 |
| | | | | 174/103 |
| 2015/0289752 | A1* | 10/2015 | Rachlin | A61B 1/00114 |
| | | | | 600/572 |
| 2016/0231561 | A1* | 8/2016 | Kasai | G02B 23/26 |
| 2017/0035404 | A1 | 2/2017 | Foster et al. | |
| 2017/0042573 | A1 | 2/2017 | Savvouras et al. | |
| 2020/0069169 | A1* | 3/2020 | Tanaka | A61C 17/022 |
| 2020/0077876 | A1 | 3/2020 | Basadonna et al. | |
| 2020/0229840 | A1* | 7/2020 | Lowe | A61B 17/320016 |
| 2021/0052214 | A1* | 2/2021 | Miyazaki | A61B 5/0059 |
| 2022/0022736 | A1* | 1/2022 | Duan | A61B 1/041 |

OTHER PUBLICATIONS

International Preliminary Report on Patentability for International Application No. PCT/US2021/041397 dated Feb. 23, 2023.

* cited by examiner

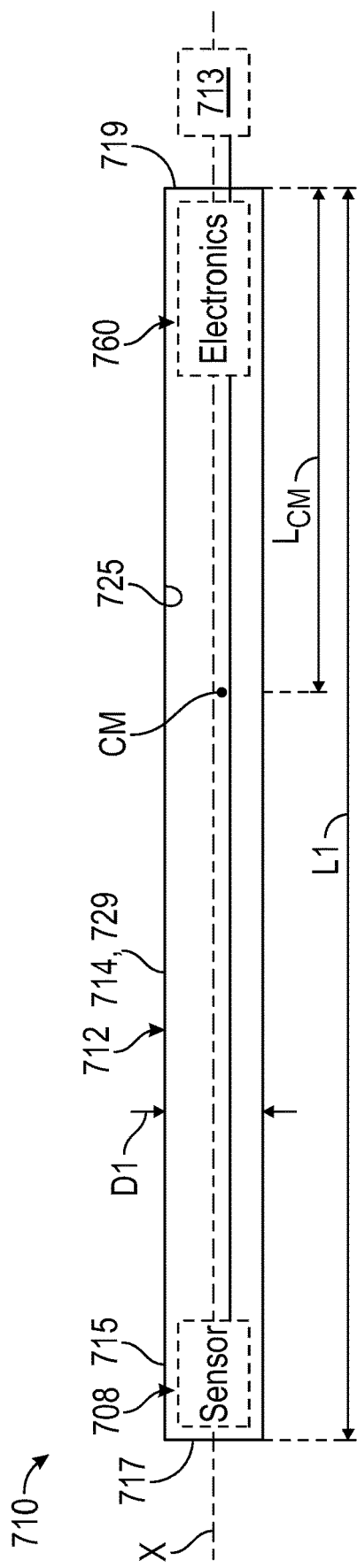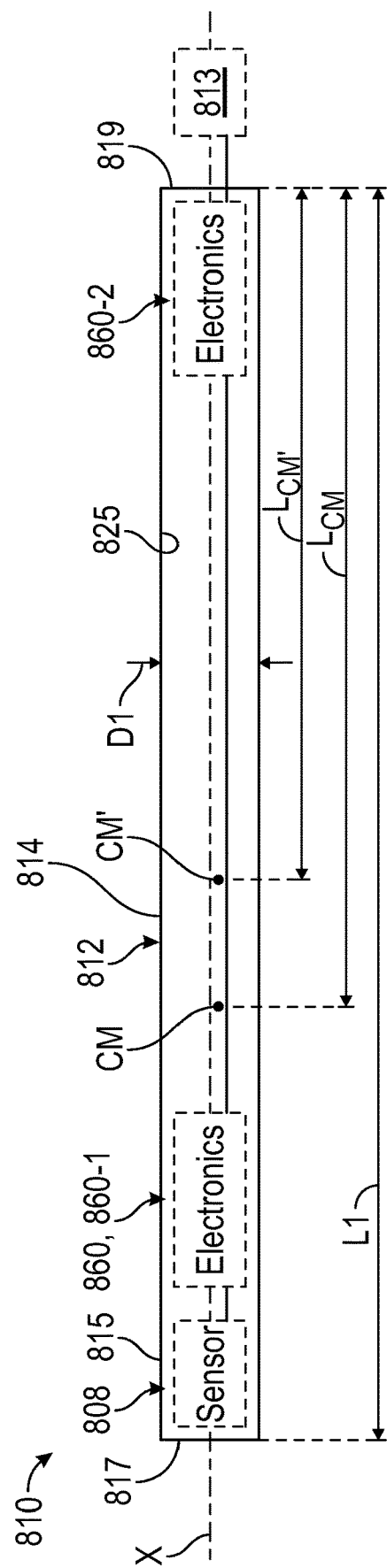

ENDOSCOPIC INSTRUMENT

CROSS-REFERENCE TO RELATED APPLICATION

This application claims priority to U.S. Provisional Application 63/065,037, filed Aug. 13, 2020, which is incorporated herein in its entirety.

BACKGROUND

This disclosure relates to surgical instruments and methods, including endoscopes and methods of performing an endoscopy.

SUMMARY

This disclosure relates to instrumentation and methods associated with performing a surgical procedure, such as an endoscopy. The instrument may be inserted into a patient. One or more images may be obtained with the instrument.

An endoscope for producing images of a surgery in vivo according to an implementation of the present disclosure includes, inter alia, a hub and an imaging rod extending from the hub. The imaging rod may be configured to receive light and direct the light to an area adjacent to a distal end of the imaging rod. An imaging sensor may be located at the distal end portion of the imaging rod. The hub and the imaging rod may be attached to form a hub assembly that may have a center of mass within the imaging rod.

An endoscope for producing images of a surgery in vivo according to an implementation of the present disclosure includes, inter alia, a communications assembly, a hub coupled to the communications assembly, and an imaging rod extending from the hub. The hub and the imaging rod may be attached to form a hub assembly having a center of mass that may be established distally of the hub. An imaging sensor may be coupled to a distal end portion of the imaging rod.

An endoscope for producing images of a surgery in vivo according to an embodiment of the present disclosure includes, inter alia, a communications assembly and a hub assembly coupled to the communications assembly. The hub assembly may include an imaging rod, an imaging sensor and electronics coupled to the imaging sensor. The imaging rod may include a main body extending a first length between a proximal end portion and a distal end portion relative to a longitudinal axis. The imaging sensor may be arranged adjacent to the distal end portion of the imaging rod. The electronics may be arranged in an internal cavity of the imaging rod. The hub assembly may have a center of mass established within the imaging rod at a second length from the proximal end portion. The second length may be greater than or equal to 50 percent of the first length.

A method of performing an endoscopy according to an implementation of the present disclosure includes, inter alia, inserting a distal end portion of an imaging rod through an insertion point of a patient, the imaging rod extending from a hub to the distal end portion, and the hub and the imaging rod attached to establish a hub assembly having a center of mass established distally of the hub, and then inserting the center of mass through the insertion point. An imaging sensor may be located at the distal end portion of the imaging rod. The method may include obtaining an image by the imaging sensor at a position inward of the insertion point subsequent to the step of inserting the center of mass.

BRIEF DESCRIPTION OF THE DRAWINGS

FIG. 12 illustrates another exemplary instrument.

FIG. 13 illustrates yet another exemplary instrument.

Like reference numbers and designations in the various drawings indicate like elements.

DETAILED DESCRIPTION

Figure 1:
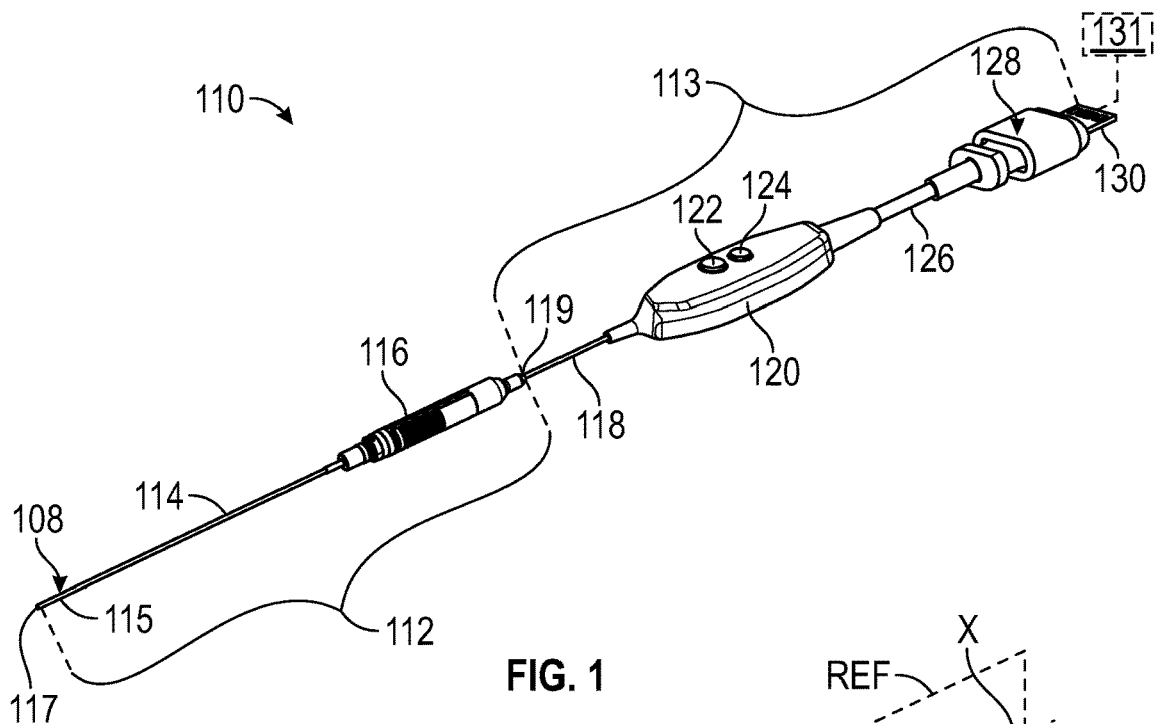
FIG. 1 illustrates a perspective view of an exemplary endoscope including a needle hub assembly and a cable assembly.

This disclosure relates to instruments and methods that may be utilized during surgical procedures such as an endoscopy. An endoscopy generally includes the insertion of a tube into the body of a patient to observe an internal organ or tissue.

An endoscope is provided with novel features. The endoscope is designed to free up the hands of the surgeon or other assistants. The endoscope may have features allowing the endoscope to be inserted into the patient and to remain in position without being held by a surgeon or assistant. A unique combination of the size, weighting, and/or form factor may allow for these attributes. The endoscope may have an electronics housing and a rod extending therefrom for insertion into the patient. The rod may include a chip attached on the distal end including an imaging sensor.

In some implementations, the chip may also include illumination elements (e.g. LED elements, fiber optic bundle, light pipe, etc.) to generate illumination in vivo. In other implementations, the illumination elements are omitted. Since the area may be flushed with fluid, the fluid may help to cool the chip which otherwise may provide heating concerns which would cause design concerns for combining the imaging sensor and the LED illumination on the same chip. The illumination elements may be configured to surround the imaging sensor and may be individually controllable. Groups of elements on the chip may have the same or different wavelengths and may be intensity controlled based on a number of factors including using image features and/or sensor features for feedback. In some implementations, one or more illumination sources may be included in a needle hub assembly as further described below.

The housing may be symmetric and balanced. For example, the housing may be cylindrical. The housing may be concentric with the rod. The housing and rod may be fixedly attached to form a single manipulatable body. The housing may have a weight that is less 2× the weight of the rod, and in some implementations less than 1.5× the weight of the rod. The housing may in some instances beneficially have a weight that is less than the weight of the rod.

The housing may have a length that is less than 0.75× the length of the rod. The housing may in some instances beneficially have a length that is less than 0.25× the length of the rod. In some instances, the components of the housing may be incorporated into the rod.

The housing may have a diameter that is less than 5× the diameter of the rod. The housing may in some instances beneficially have a diameter that is the same or less than the diameter of the rod.

The combined body of the housing and rod may have a center of mass that is located distally from the housing, for example within the rod. As such, the center of mass may be configured to be within the body of the patient when inserted during an operation. Having the center of mass in the rod and/or inside the patient may allow the endoscope to remain more securely in place without intervention from the surgeon or assistant.

The housing may communicate wirelessly with a display or control device. Alternatively, the housing may have a length of cable that is greater than 1.5 feet from the housing to a control/display device allowing the body to be positioned with sufficient cable slack to negate or otherwise reduce any cable tension affecting the end of the housing and causing a force acting at an angle to the central axis of the endoscope that would cause the endoscope to tip off axis.

An endoscope for producing images of a surgery in vivo according to an implementation of the present disclosure includes, inter alia, a hub and an imaging rod extending from the hub. The imaging rod may be configured to receive light and direct the light to an area adjacent to a distal end of the imaging rod. An imaging sensor may be located at the distal end portion of the imaging rod. The hub and the imaging rod may be attached to form a hub assembly that may have a center of mass within the imaging rod.

In a further implementation, the imaging rod may extend a first length between the distal end portion and an interface between the imaging rod and the hub. The center of mass may be established within the imaging rod at a second length from the interface. The second length may be greater than or equal to 10 percent of the first length.

In a further implementation, the hub may include electronics configured to transmit image data from the imaging sensor.

In a further implementation, the second length may be greater than or equal to 25 percent of the first length.

In a further implementation, the hub may include a light supply.

In a further implementation, the hub may include a power supply.

In a further implementation, the hub may include electronics configured to transmit image data wirelessly.

In a further implementation, the hub may include electronics configured to transmit image data digitally.

In a further implementation, the hub may include electronics configured to transmit image data across a coaxial cable in an analog signal.

In a further implementation, the hub assembly may be symmetric with respect to a reference plane extending along a longitudinal axis of the hub assembly.

In a further implementation, the hub may be cylindrical.

In a further implementation, a length of the hub may be less than 0.75× of a length of the imaging rod.

In a further implementation, a diameter of the hub may be less than 5× of a diameter of the imaging rod.

In a further implementation, a weight of the hub may be less than 2× of a weight of the imaging rod.

In a further implementation, the hub may include electronics including an electronic circuit, a light supply and an optical coupler. The electronic circuit may be configured to transmit image data from the imaging sensor. The light supply may be connected to the electronic circuit. The light supply may be configured to generate illumination in vivo, The optical coupler may be configured to communicate light from the light supply to a fiber optic. The fiber optic may be configured to transmit light from the hub to the distal end portion of the imaging rod. An enclosure may be configured to enclose the electronic circuit, the light supply and the optical coupler. A hub coupler may connect the imaging rod to the enclosure.

In a further implementation, a cable assembly may include a first cable, a second cable, a connector and a button yoke having one or more controls. The first cable may be coupled to a proximal end portion of the hub assembly. The button yoke may interconnect the first and second cables. The second cable may interconnect the button yoke and the connector. The connector may have a terminal configured to interface with the external device.

An endoscope for producing images of a surgery in vivo according to an implementation of the present disclosure includes, inter alia, a communications assembly, a hub coupled to the communications assembly, and an imaging rod extending from the hub. The hub and the imaging rod may be attached to form a hub assembly having a center of mass that may be established distally of the hub. An imaging sensor may be coupled to a distal end portion of the imaging rod.

In a further implementation, the center of mass may be established within the imaging rod.

In a further implementation, a light source may be within the imaging rod adjacent to the distal end portion.

In a further implementation, the hub may include an enclosure configured to enclose electronics.

In a further implementation, a plurality of light sources may be configured in an array to surround the imaging sensor.

In a further implementation, the plurality of light sources may be respective pathways configured to branch from a common light source.

In a further implementation, the light sources may be individually controllable.

An endoscope for producing images of a surgery in vivo according to an embodiment of the present disclosure includes, inter alia, a communications assembly and a hub assembly coupled to the communications assembly. The hub assembly may include an imaging rod, an imaging sensor and electronics coupled to the imaging sensor. The imaging rod may include a main body extending a first length between a proximal end portion and a distal end portion relative to a longitudinal axis. The imaging sensor may be arranged adjacent to the distal end portion of the imaging rod. The electronics may be arranged in an internal cavity of the imaging rod. The hub assembly may have a center of mass established within the imaging rod at a second length from the proximal end portion. The second length may be greater than or equal to 50 percent of the first length.

In a further implementation, the second length may be greater than 50 percent of the first length.

In a further implementation, the electronics may be arranged adjacent to the distal end portion of the imaging rod.

In a further implementation, the second length may be greater than 75 percent of the first length.

A method of performing an endoscopy according to an implementation of the present disclosure includes, inter alia, inserting a distal end portion of an imaging rod through an insertion point of a patient, the imaging rod extending from a hub to the distal end portion, and the hub and the imaging rod attached to establish a hub assembly having a center of mass established distally of the hub, and then inserting the center of mass through the insertion point. An imaging sensor may be located at the distal end portion of the imaging rod. The method may include obtaining an image by the imaging sensor at a position inward of the insertion point subsequent to the step of inserting the center of mass.

In a further implementation, the center of mass may be established within the imaging rod.

In a further implementation, the hub may be outward of the insertion point during the obtaining step.

In a further implementation, the method may include releasing the hub assembly such that the center of mass may be in vivo. The method may include releasing the hub assembly such that the hub may be substantially cantilevered from the imaging rod outward of the insertion point.

In a further implementation, a length of the hub may be less than 0.75× of a length of the imaging rod. A weight of the hub may be less than 2× of a weight of the imaging rod.

In a further implementation, the method may include communicating light to the imaging sensor prior to the obtaining step.

In a further implementation, the communicating step may include communicating the light from the hub, then through the imaging rod, and then towards an area adjacent to the distal end portion of the imaging rod.

In a further implementation, the communicating step may include communicating the light from a plurality of light sources adjacent to the distal end portion of the imaging rod. The light sources may be configured in an array to surround the imaging sensor.

In a further implementation, the communicating step may include individually controlling the light sources to communicate the light.

In a further implementation, the insertion point may be established by an incision in skin of the patient.

FIGS. 1-4 illustrate an exemplary endoscope 110, which may be utilized to produce images of a surgery in vivo. Referring to FIG. 1, the endoscope 110 may include a needle hub assembly 112 and a cable (e.g., communications) assembly 113. The needle hub assembly 112 may include a scope 114 (e.g., a camera or imaging rod) secured in a needle hub 116, as illustrated in FIGS. 1 and 2B. The scope 114 extends from a distal end of the needle hub 116. The scope 114 and needle hub 116 can be dimensioned such that the needle hub assembly 112 is substantially symmetrical (e.g., mirror symmetry) with respect to a reference plane REF that extends along a longitudinal (e.g., central) axis X of the assembly 112 to divide the assembly 112 into two opposed portions, as illustrated in FIGS. 2A-2B.

Figure 2A:
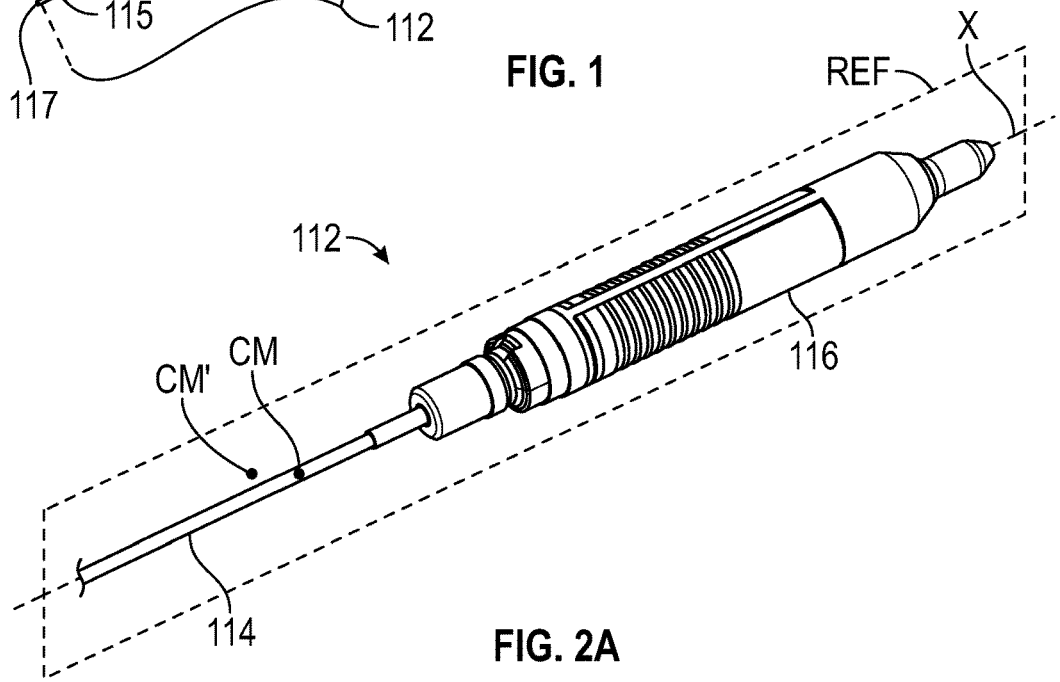
FIG. 2A illustrates a perspective view of the needle hub assembly of FIG. 1.
Figure 2B:
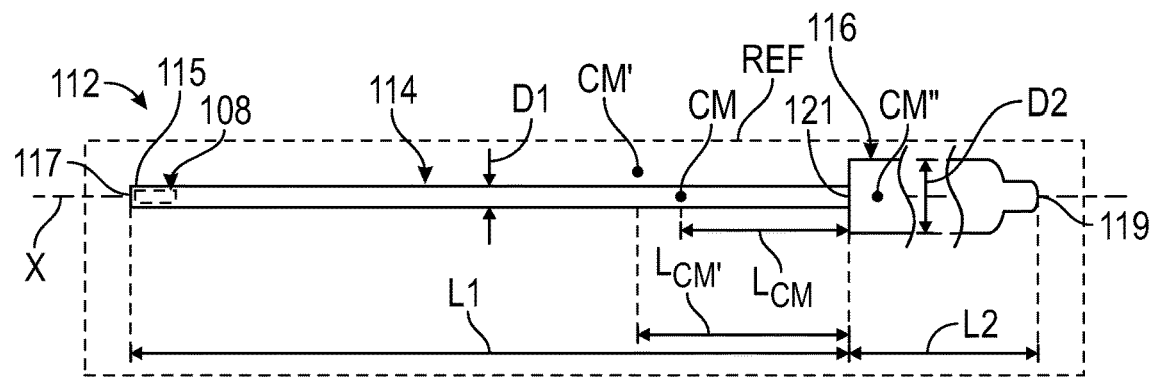
FIG. 2B illustrates a side view of the needle hub assembly of FIG. 1.

Various techniques may be utilized to dimension the hub assembly 112. Referring to FIG. 2B, with continuing reference to FIGS. 1 and 2A, the scope 114 may extend a first length L1 between the terminal (e.g., distal) end 117 and an interface 121 between the scope 114 and the distal end of the hub 116 relative to the longitudinal axis X. The interface 121 may be established at or adjacent to a proximal end of the scope 114. In implementations in which the scope 114 is flexible, the first length L1 corresponds to a maximum configurable length of the scope 114. In implementations in which the hub 116 is omitted, the first length L1 may be established between the proximal and distal ends of the scope 114. In implementations, the first length L1 may be between approximately 100 millimeters (mm) and 300 mm. The needle hub 116 may extend a second length L2 between opposed proximal and distal ends of the needle hub 116 relative to the longitudinal axis X. The scope 114 may establish a first diameter D1. The needle hub 116 may establish a second diameter D2. The first and second lengths L1, L2 and/or first and second diameters D1, D2 may be the same or may differ. In some implementations, the length L2 of the needle hub 116 is less than 0.75× of the length L1 of the scope 114, the diameter D2 of the hub 116 is less than 5× of the diameter D1 of the scope 114, and/or a weight of the hub 116 is less than 2× of a weight of the scope 114.

The hub 116 and scope 114 can be attached to form the hub assembly 112 having a center of mass CM. The center of mass CM may be established at a longitudinal position relative to the longitudinal axis X. The longitudinal position of the center of mass CM may be aligned with a longitudinal position along the scope 114 relative to the longitudinal axis X. The center of mass CM may be established distally of the needle hub 116 relative to the longitudinal axis X. In implementations, the center of mass CM may be established within the scope 114 along the longitudinal axis X. In other implementations, the needle hub assembly 112 may be configured such that the center of mass may be established adjacent to, but offset from, the scope 114, as illustrated by center of mass CM' (FIG. 2A). The endoscope 110 may be configured such that the center of mass CM may be inside or outside of the patient during a surgical procedure.

The hub 116 and/or scope 114 may be symmetric or asymmetric to establish the center of mass CM. For example, the scope 114 may have a curvilinear geometry such that one or more portions of the scope 114 are offset from the longitudinal axis X to establish an asymmetric configuration. As another example, component(s) within the hub 116 may be arranged such that a center of mass of the component(s) are offset from the longitudinal axis X.

The center of mass CM may be established at various positions relative to the scope 114 and/or needle hub 116. The hub assembly 112 may be configured such that a portion of the hub assembly 112 including the center of mass CM may be positioned in a patient to improve retention of the endoscope 110 without intervention by the surgeon or assistant, although another other portion of the hub assembly 112 may be positioned outside of the patient. The center of mass CM may established at, adjacent to, or distally of the distal end of the needle hub 116.

The center of mass CM may be established at a distance $L_{CM}$ from a proximal boundary of the first length L1. The proximal boundary of the first length L1 may be established by the interface 121 between the scope 114 and the distal end of the hub 116 or may be established by a proximal end of the scope 114 for implementations in which the hub 116 is omitted. The hub assembly 112 may be configured such that a center of mass CM' is offset from the scope 114. The distance $L_{CM}$ may be less than 10 percent of the first length L1. The center of mass CM may established at the interface 121 between the scope 114 and the distal end of the needle hub 116. In implementations, center of mass CM" may be established proximal of the interface 121 within the hub 116. The hub assembly 112 may be configured such that the distance $L_{CM}$ is greater than or equal to 10 percent of the first length L1, or more narrowly greater than or equal to approximately 25 percent of the first length L1. In implementations, the distance $L_{CM}$ may be less than or equal to approximately 50 percent of the first length L1. For the purposes of this disclosure, the terms "substantially," "approximately" and "about" mean±10 percent of the stated value or relationship unless otherwise indicated. Utilizing the techniques disclosed herein, including the disclosed dimensional relationships and distributions, the surgeon or assistant may position the hub assembly 112 in vivo in a manner that reduces a likelihood of movement or intervention while the endoscope 110 is not being held.

Figure 3:
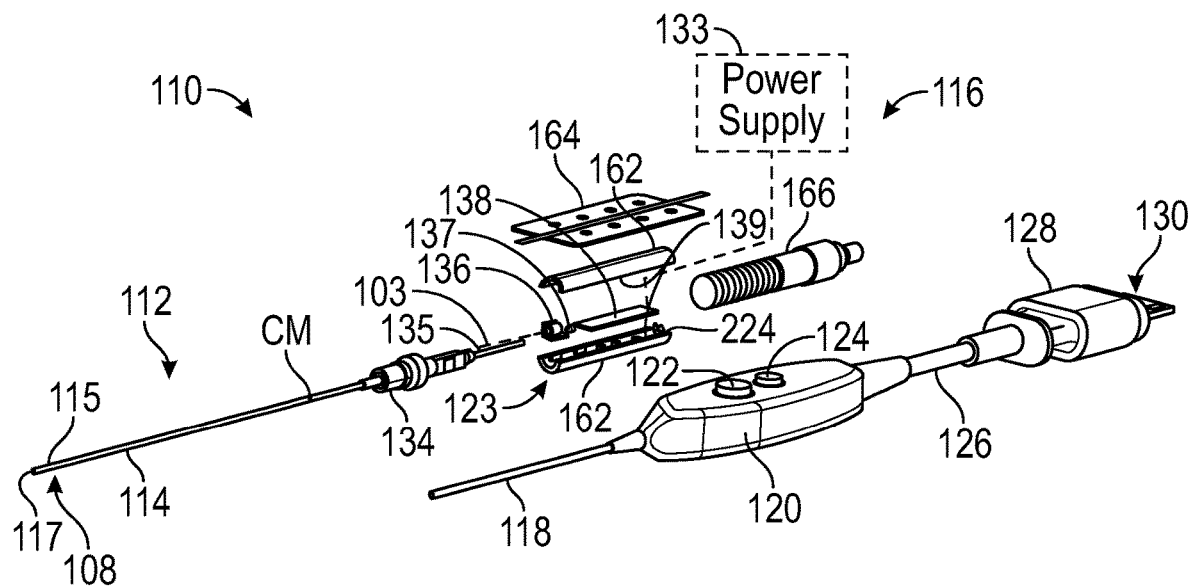
FIG. 3 illustrates an exploded view of the endoscope of FIG. 1.

Referring to FIG. 3, with continuing reference to FIG. 1, the cable assembly 113 may include a first cable 118 (e.g. a micro coaxial cable), a button yoke 120, a second cable 126, and a connector 128. The connector 128 may include a terminal 130 configured to communicate with an external device, such as a display or control device 131 (shown in dashed lines in FIG. 1 for illustrative purposes). In other implementations, the endoscope 110 communicates wirelessly with the control device 131. The needle hub assembly 112 or the cable assembly 113 can include a power supply 133 that provides power to the various electrical components of the endoscope 110 in operation (shown in dashed lines in FIG. 3 coupled to electronic circuit 138 for illustrative purposes). In other implementations, power is provided by an external device and is communicated by the terminal 130 to the various electrical components.

The scope 114 can include an imaging sensor 108 located on, at or otherwise adjacent to a distal end portion 115 of the scope 114 for obtaining images of a surgical site. The imaging sensor 108 may be a sensor assembly including a sensor and optics. The scope 114 can be configured to receive light and direct the light to or otherwise towards an area (e.g., scene or space being viewed by the surgeon) adjacent to the distal end portion 115 of the scope 114. The light may be reflected from the area back towards the sensor 108.

The scope 114 and each cable 118, 126 may be relatively rigid or flexible. The distal end portion 115 of the scope 114 establishes a terminal end 117 (e.g., tip) of the endoscope 110. At least a portion of the scope 114 including the distal end portion 115 can be relatively flexible or bendable, and may comprise a Nitinol material, for example. Configuring the scope 114 to be relatively flexible can facilitate orienting the sensor 108 including bending or steering the sensor 108 around corners and viewing various angles of the surgical site, for example.

Figure 4:
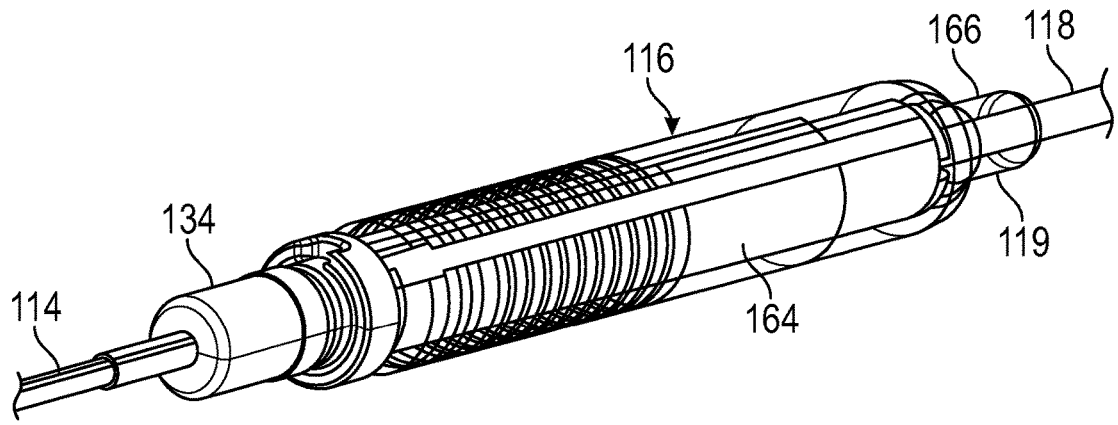
FIG. 4 illustrates a perspective view of the needle hub assembly of FIG. 1, including a support boot shown in phantom.

The first cable 118 may be a coaxial cable (e.g. a micro coax cable). The first cable 118 may be coupled to a proximal end portion 119 of the hub assembly 112, as illustrated in FIGS. 1 and 4. In some implementations, the first cable 118 may communicate analog signals between the needle hub 116 and the button yoke 120. The button yoke 120 may interconnect the first cable 118 and the second cable 126. The second cable 126 may interconnect the button yoke 120 and the connector 128.

The button yoke 120 may have one or more controls (e.g. buttons, dials, levers, etc.) such as button 122 and button 124, for example. Each button 122, 124 may have one or more functions, such as image and video capture. Each button 122, 124 may be programmable for a number of functions. Additionally, multiple functions can be accessed based on the number of times a button 122, 124 is pressed, the amount of time within which the button 122, 124 is pressed multiple times, and/or the amount of time for which a button 122, 124 remains depressed continuously.

The first and second cables 118, 126 can have various dimensions. In some implementations, the second cable 126 has a length of approximately 2 feet, which may allow the button yoke 120 to rest on a surface when the endoscope 110 is in use and may minimize or otherwise reduce the effect on the stationary position of the hub 116.

The needle hub 116 may include a hub coupler 134 that connects the scope 114 to other components of the needle hub 116. The needle hub 116 may include various electronics 123 including a flexible circuit board 135, the electronic circuit 138, a light supply 137 and an optical coupler 136. The flexible circuit board 135 may extend from the needle hub 116 through the scope 114 to the sensor 108. The flexible circuit board 135 may be connected to the electronic circuit 138. The electronic circuit 138 may be in the form of a printed circuit board and may include one or more chips. The electronic circuit 138 can be configured to transmit image data across a coaxial cable, such as the first cable 118, in an analog signal. In implementations, one or more of the electronics 123 may be incorporated into the button yoke 120, including the power supply 133, flexible circuit board 135, optical coupler 136, light supply 137 and/or electronic circuit 138, and a separate hub 116 including the enclosure 139 may be omitted.

The scope 114 can be configured to receive light and direct the light to or towards an area adjacent to the distal end portion 115 of the scope 114. The light may be directly or indirectly communicated from the scope 114 to the sensor 108. For example, the light may be reflected from the area back to or otherwise towards the sensor 108. The circuit 138 and/or flexible circuit board 135 may be connected to the light supply 137 (e.g., light source or illumination element). The light source 137 may be a light emitting diode (LED), for example, and can be configured and utilized to generate illumination in vivo. The optical coupler 136 may be configured to communicate light from the light source 137 to a fiber optic (e.g., light pipe) 103 (shown in dashed lines in FIG. 3 for illustrative purposes). The fiber optic 103 may be configured to transmit the light from the needle hub 116 to the distal end portion 115 of the scope 114. In other implementations, the fiber optic 103 may be omitted and the light source 137 may be positioned within the scope 114 distally of the needle hub 116. In implementations, a separate light source may be situated externally but adjacent to the distal end portion 115 of the scope 114 to illuminate the surgical site.

Figure 6:
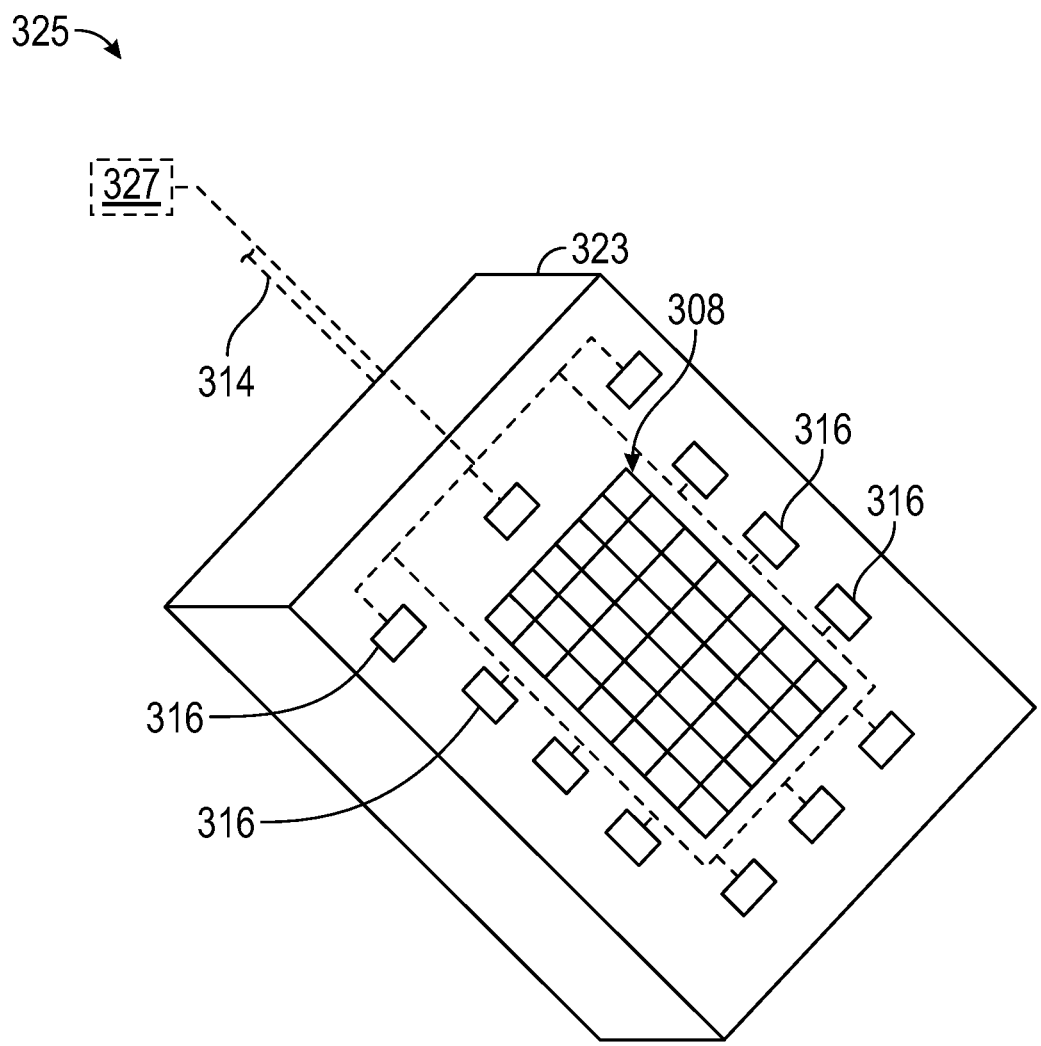
FIG. 6 illustrates an exemplary electronical component.

In some implementations, imaging sensor 308 and one or more light sources 316 are integrated with or mounted to a common circuit board 323 (e.g., chip) to establish an electrical component 325, as illustrated in FIG. 6. The light sources 316 can be configured in an array to surround the sensor 308 and may be individually controllable. In implementations, the light sources 316 may be respective pathways configured to branch from a singular, common light source 327 (shown in dashed lines for illustrative purposes). The light sources 316 may be utilized to improve communication of light in a relatively compact arrangement. The common light source 327 may be coupled to the circuit board 323 or another portion of the endoscope. Groups of light sources 316 on the circuit board 323 may have the same or different wavelengths and may be intensity controlled based on a number of factors including using image features and/or sensor features for feedback. The electrical component 325 can be situated at any of the positions of the image sensors disclosed herein. For example, the electrical component 325 can be coupled or attached on or adjacent to the distal end portion 115 of the scope 114 (FIG. 1). Combining the imaging sensor 308 and light source(s) 316 on the same circuit board 323 may improve cooling augmentation by fluid conveyed to a surgical site, such as fluid utilized to flush the surgical site during a surgical procedure.

The various electronics of the needle hub assembly 112 can be configured to transmit image data wirelessly and/or digitally from the imaging sensor 108 to an external device, such as the control device 131, and/or another component of the endoscope 110, such as the button yoke 120. Other sensors can be incorporated into the endoscope 110. For example, one or more sensors may be configured to sense or measure various conditions at the distal end portion 115 of the scope 114, such as temperature sensors, pressure sensors, etc. In some implementations, an accelerometer and/or gyroscope is positioned in the needle hub 116 and/or scope 114 to sense a change in position and/or orientation of the endoscope 110.

Figure 7:
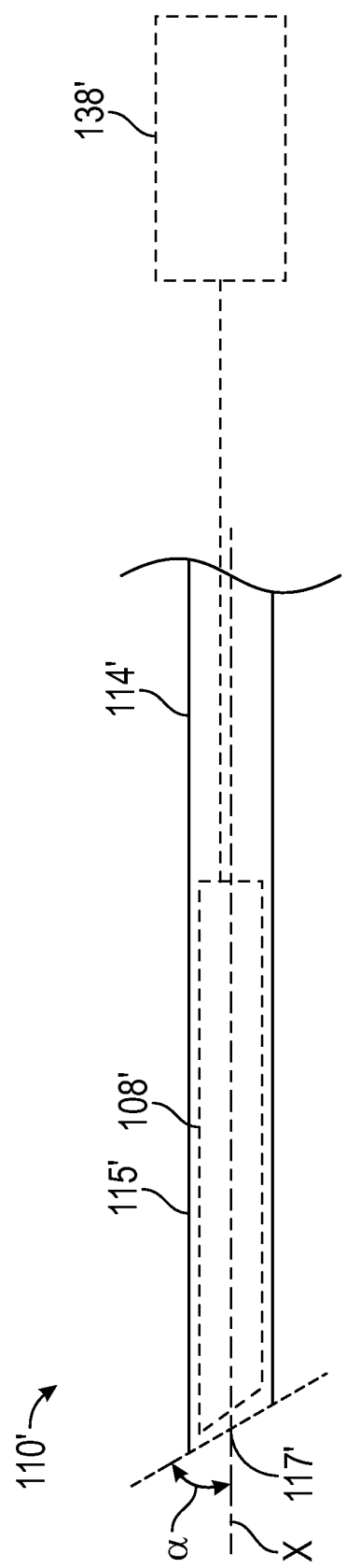
FIG. 7 illustrates another exemplary endoscope.

The terminal end 117 of the distal end portion 115 can be established at various angles relative to a central or longitudinal axis of the endoscope 110. For, example, the terminal end 117 can be substantially perpendicular to the longitudinal axis X of the scope 114, as illustrated in FIGS. 1 and 2A-2B. In some implementations, a terminal end 117' of distal end portion 115' establishes an angle α that is transverse to a central or longitudinal axis X of the scope 114', as illustrated in FIG. 7. A sensor image obtained by sensor 108' can be oriented at an angle (e.g., 30 degrees) corresponding to the angle α, for example. Electronic circuit 138' or another portion of endoscope 110' can be programmed with or otherwise incorporate logic to perform a correction or translation of the captured image(s) to reorient the captured image(s) as the sensor 108' rotates during a procedure.

Referring still to FIG. 3, the needle hub 116 may include an enclosure 139 configured to enclose components of the needle hub 116. The enclosure 139 may include a first shell 162 and a second shell 164 that cooperate to enclose the electronics and other components of the needle hub 116 (e.g., light source 137, circuit 138, and optical coupler 136). The hub coupler 134 may couple the scope 114 to the shells 162 and 164 of the enclosure 139. The hub coupler 134 may be a separate and distinct component or may be incorporated into the enclosure 139 and/or the scope 114.

A shield 230 may at least partially or completely surround the enclosure 139, as illustrated in FIG. 4. The shield 230 may take the form of a flexible shield and may be formed of a conductive material such as copper. Accordingly, the shield 230 may take the form of a copper foil. A support boot 166 may support the enclosure 139 and the first cable 118, as illustrated in FIG. 4 (shown in phantom).

Figure 5:
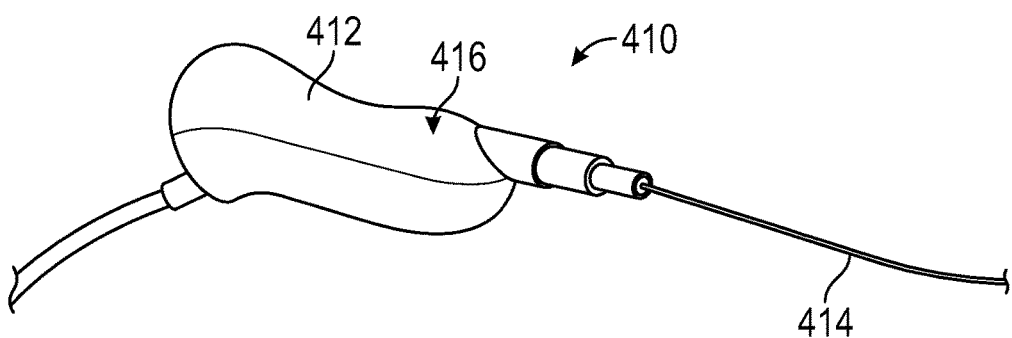
FIG. 5 illustrates a perspective view of another exemplary endoscope.

For comparison purposes, FIG. 5 illustrates another exemplary endoscope 410. The endoscope 410 may have a handpiece 412 and a camera rod 414. The handpiece 412 may be designed to be held by the surgeon or an assistant and to include all of the control electronics. In these implementations a center of mass of the endoscope 410 could be significantly back in the handpiece 412 and therefore may be held more extensively by the assistants rather than being staying static without being guided by the assistant.

Figure 8:
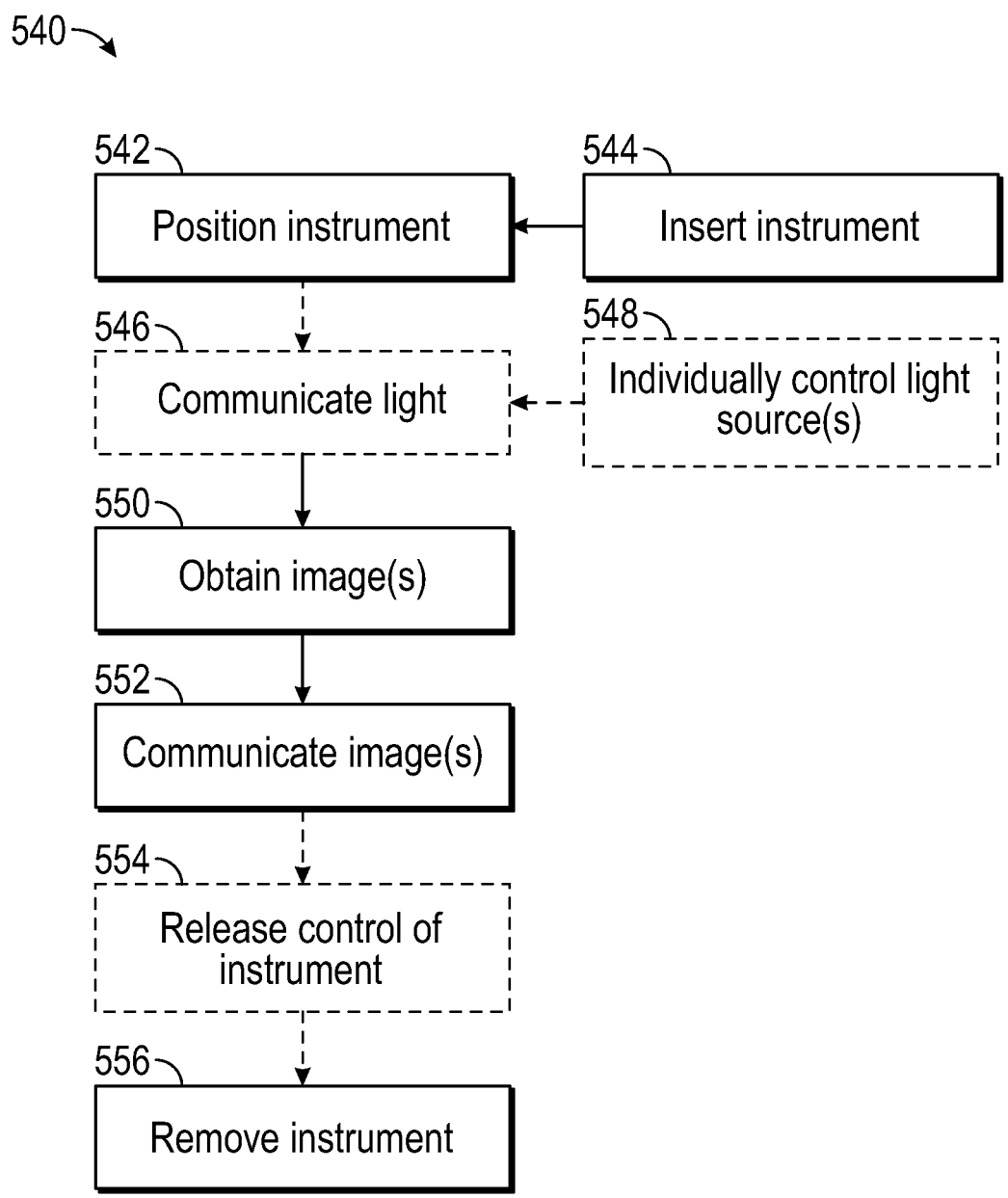
FIG. 8 illustrates a method in a flowchart of performing a surgical procedure.

FIG. 8 illustrates an exemplary method of performing a surgical procedure in a flowchart 540. The method 540 may be utilized to perform an endoscopy. The method 540 can be utilized with any of the instruments and assemblies disclosed herein, including the endoscopes 110, 110' and endoscopes 710, 810 (FIGS. 12-13). Obtained images may be utilized pre-operatively, inter-operatively, and/or post-operatively and may be utilized in conducting various surgical procedures, such as an arthroplasty to restore functionality to a joint. Fewer or additional steps than are recited below could be performed within the scope of this disclosure, and the recited order of steps is not intended to limit this disclosure. Reference is made to instrument (e.g., endoscope) 610 of FIGS. 9-11 for illustrative purposes.

Figure 9:
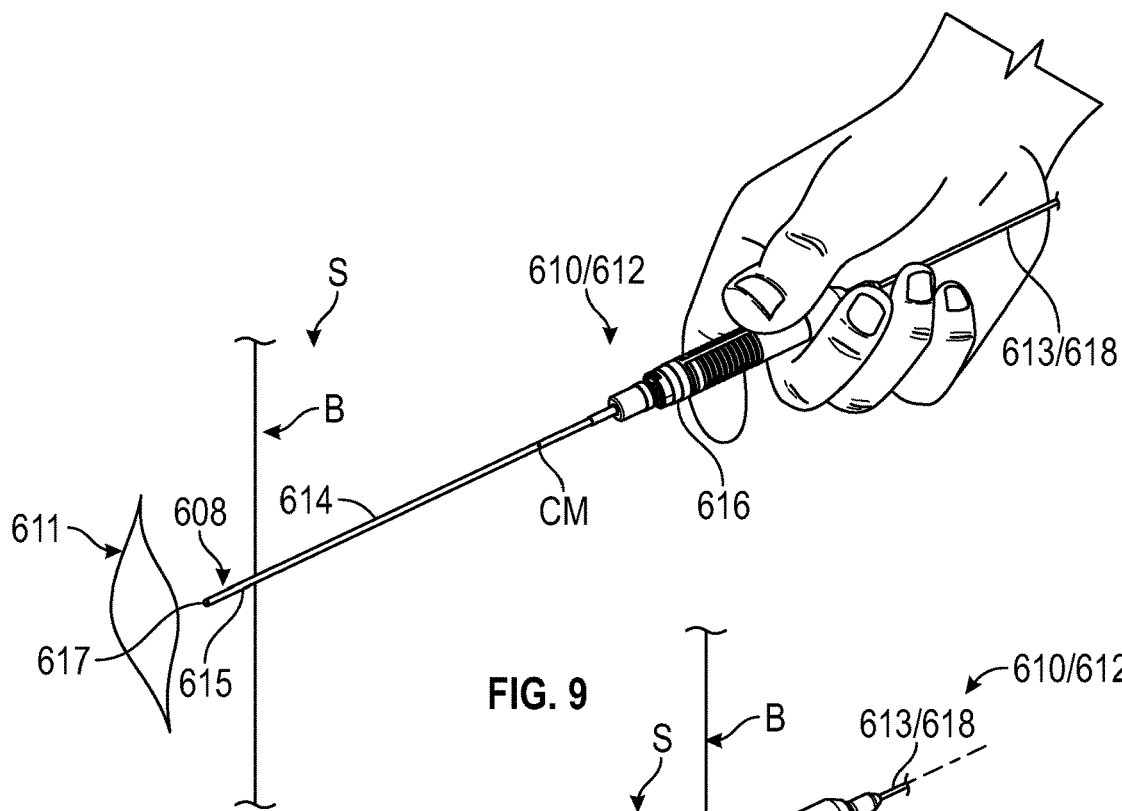
FIG. 9 illustrates an instrument positioned adjacent to an insertion point of a patient.
Figure 10:
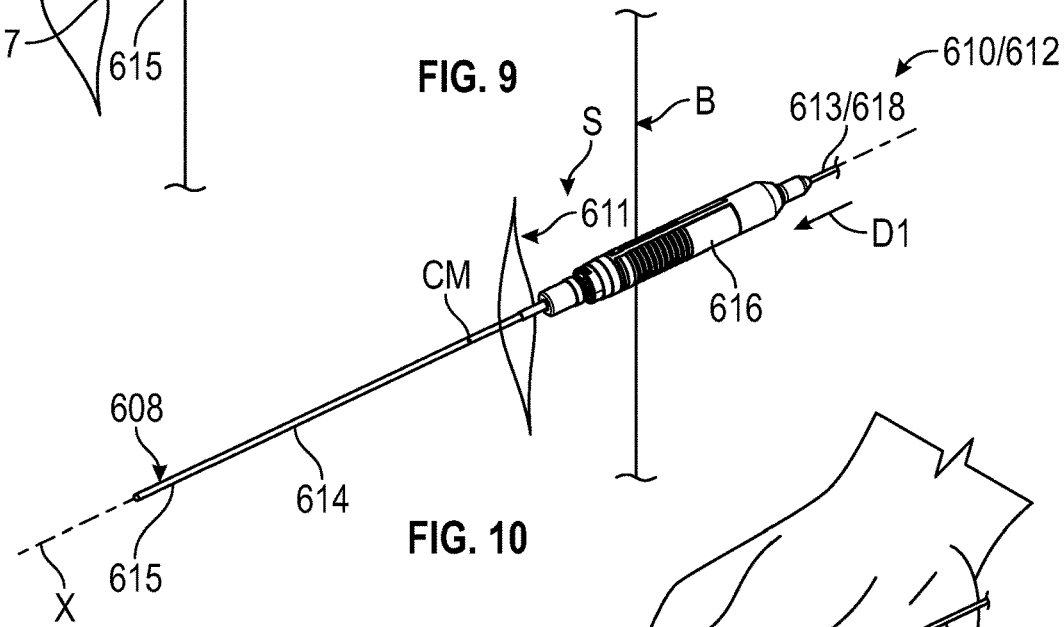
FIG. 10 illustrates a portion of the instrument inserted through the insertion point of FIG. 9.

Referring to FIG. 9, with continuing reference to FIG. 8, the instrument 610 may include a hub assembly 612 coupled to a cable assembly 613. The hub assembly 612 may include a hub 616 and a scope 614 (e.g., a camera or imaging rod) coupled to the hub 616. The hub 616 may have a generally or substantially tubular geometry and may serve as a handle to position the hub assembly 612. The hub assembly 612 may include an imaging sensor 608 located at a distal end portion 615 of the imaging rod 614. The imaging rod 614 may extend from the hub 616 to the distal end portion 615. The hub 616 and the imaging rod 614 may be attached to establish the hub assembly 612 having a center of mass CM. The center of mass CM may be established distally of the hub 616 relative to a longitudinal axis X of the hub assembly 612 (FIG. 10). The hub assembly 612 may be configured such that the center of mass CM may be established within or adjacent to the imaging rod 614. The hub assembly 612 may be configured according to any of the techniques disclosed herein. In implementations, a length of the hub 616 may be less than 0.75× of a length of the imaging rod 614, a weight of the hub 616 may be less than 2× of a weight of the imaging rod 614 and/or a diameter of the hub 616 may be less than 5× of a diameter of the imaging rod 614.

At step 542, the instrument 610 may be positioned relative to an insertion point 611 in a body B of a patient at a surgical site S. The insertion point 611 may be an incision made through skin, an orifice, or another opening in the body B of the patient. Method 540 may include forming the incision prior to step 542.

Referring to FIG. 10, with continuing reference to FIGS. 8-9, step 542 may include moving the instrument 610 in a direction D1, and then inserting a portion of the instrument 610 through the insertion point 611 at step 544. Step 544 may occur such that the portion of the instrument 610 is situated in vivo. Step 544 may include inserting at least the distal end portion 615 of the imaging rod 614 through the insertion point 611 of the patient, and then then inserting the center of mass CM of the instrument 610 through the insertion point 611. A portion of the hub assembly 612 including the center of mass CM may be positioned within the patient, while another portion of the hub assembly 612 may be positioned outside of the patient, such as the hub 616 and/or a portion of the imaging rod 614 proximal of the center of mass CM including a proximal end of the imaging rod 614.

At step 546, the method 540 may include communicating light to the imaging sensor 608. Various techniques may be utilized to communicate light to the imaging sensor 608. In implementations, step 546 may include communicating the light from the hub 616, then through the imaging rod 614, and then to an area of the patient adjacent the distal end portion 615 of the imaging rod 614. The light may be reflected from the area back to or otherwise towards the imaging sensor 608 (see also hub 116, imaging sensor 108 and imaging rod 114 of FIG. 1). In implementations, step 546 may include communicating the light from one or more light sources adjacent the distal end portion 615 of the imaging rod 614. The light sources may be configured in an array to surround the imaging sensor 608 (see, e.g., imaging sensor 308 and light sources 316 of FIG. 6). Step 546 may include individually controlling the light sources to communicate the light at step 548.

At step 550, the surgeon or assistant may cause the instrument 610 to obtain one or more images by the imaging sensor 608 at a position inward of the insertion point 611. Step 550 may occur subsequent to positioning the instrument 610 at step 542 and/or communicating the light at step 546. The center of mass CM of the instrument 610 may be inward of the insertion point 611 or otherwise situated in vivo, and the hub 116 may be situated outward of the insertion point 611 or otherwise situated ex vivo during obtaining the image(s) at step 550. At step 552, the image(s) may be communicated to an external device (see, e.g., external device 131 of FIG. 1).

At step 554, the surgeon or assistant may release control of the instrument 610 while the distal end portion 615, imaging sensor 608 and/or center of mass CM of the instrument 610 are situated in vivo, as illustrated in FIG. 10. Step 554 may include releasing control of the hub assembly 612 such that the center of mass CM may be situated in vivo and such that the hub 116 may be substantially cantilevered from the imaging rod 614 outward of the insertion point 611. For the purposes of this disclosure, the term "substantially" cantilevered means that no more than 10 percent of the hub assembly 112 outward of the insertion point 611 is supported by means other than the imaging rod 614. Step 554 may include balancing the hub assembly 612 at or otherwise adjacent to the insertion point 611 in response to releasing control of the hub assembly 612. The instrument 610 may remain in position without being held or otherwise supported by a surgeon or assistant, which may improve flexibility and decrease time in performing other steps in a surgical procedure.

Figure 11:
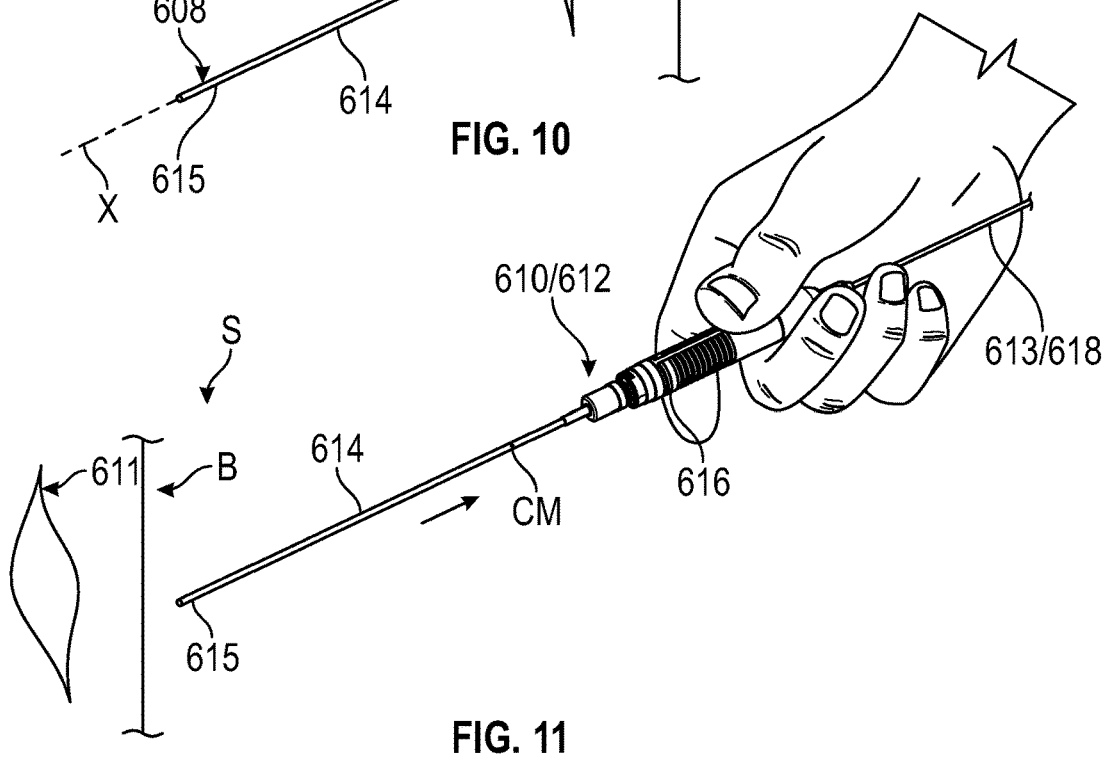
FIG. 11 illustrates the portion of the instrument withdrawn from insertion point of FIG. 10.

Referring to FIG. 11, with continuing reference to FIG. 8, at step 556 the portion of the instrument 610 that is situated in vivo may be moved in a direction D2 until the instrument 610 is withdrawn from the insertion point 611 and removed from the patient. Step 556 may include withdrawing the imaging sensor 608, distal end portion 615 and center of mass CM of the instrument 610 from the patient.

FIG. 12 illustrates another exemplary instrument 710. The instrument 710 may be an endoscope utilized to obtain one or more images of a surgical site. The instrument 710 may include a needle hub assembly 712 coupled to a cable (e.g., communications) assembly 713 (shown in dashed lines for illustrative purposes). In the implementation of FIG. 12, a separate hub is omitted from the hub assembly 712.

The hub assembly 712 may include a scope 714 (e.g., a camera or imaging rod). The scope 714 may include a main body 729 extending along a longitudinal axis X between a distal end portion 715 and a proximal end portion 719 of the hub assembly 712. The main body 729 may have a generally or substantially tubular geometry and may establish an internal cavity 725. The scope 714 may establish a first diameter D1. The main body 729 may be dimensioned such that the first diameter D1 is substantially constant between the distal end portion 715 and proximal end portion 719 of the of the scope 714.

The scope 714 can include an imaging sensor 708 configured to obtain images of a surgical site. The imaging sensor 708 may be arranged within the internal cavity 725 and may be arranged at the distal end portion 715 of the scope 714 to obtain one or more images of a surgical site. The surgeon or assistant may utilize a portion of the scope 714 as a handle to situate the imaging sensor 708 at a desired position and orientation within the patient.

The hub assembly 712 may include various electronics 760, including any of the electronics disclosed herein, such as a flexible circuit board, electronic circuit, light supply, optical coupler and/or power supply (see, e.g., FIG. 3). The electronics 760 may be integrated onto a single chip to establish an electronics unit, which may integrate or may be coupled to the imaging sensor 708. The electronics 760 may be arranged at various positions within the cavity 725 of the scope 714. The electronics 760 may be arranged proximal of a center of mass CM of the hub assembly 712, such as at or adjacent to the proximal end portion 719 of the scope 714. The electronics 760 may include a light source within the scope 714 adjacent to the proximal end portion 719.

The center of mass CM may be established at a longitudinal position between the distal and proximal end portions 715, 719 of the hub assembly 712, including within the scope 714. The center of mass CM may be established at a distance $L_{CM}$ from a proximal boundary of a first length L1 of the scope 714. The hub assembly 712 may be configured such that the center of mass CM is established according to any of the ratios of the distance $L_{CM}$ and first length L1 disclosed herein. In implementations, the hub assembly 712 may be configured such that the distance $L_{CM}$ is greater than or equal to 25 percent of the first length L1, or more narrowly greater than or equal to approximately 50 percent of the first length L1. In implementations, the distance $L_{CM}$ may be less than or equal to approximately 75 percent of the first length L1.

Arranging at least some, a majority of, or all electronics 760 and/or other internal components of the hub assembly 712 into the scope 714 may be utilized to shift a center of mass CM of the hub assembly 712 relatively more distally relative to the proximal end portion 719 of the hub assembly 712, which may improve retention of the instrument 710 without intervention by the surgeon or assistant.

FIG. 13 illustrates another exemplary instrument 810. The instrument 810 may be an endoscope utilized to obtain one or more images of a surgical site. The instrument 810 may include a hub assembly 812 coupled to a cable (e.g., communications) assembly 813. In the implementation of FIG. 13, a separate hub is omitted.

The instrument 810 may include various electronics 860 arranged at various positions within a cavity 825 of the scope 814. The electronics 860 may include a first set of electronics 860-1 and a second set of electronics 860-2, which may include any of the electronics disclosed herein.

The electronics 860 may be distributed within the scope 814 to establish a center of mass CM at various locations between a distal end portion 815 and proximal end portion 819 of the hub assembly 812. The center of mass CM may be established at a longitudinal position between the distal and proximal end portions 815, 819, including within the scope 814. The first set of electronics 860-1 may be arranged distal of the center of mass CM of the hub assembly 812. The second set of electronics 860-2 may be arranged proximal of the center of mass CM. The first set of electronics 860-1 may be arranged at or adjacent to the distal end portion 815 of the scope 814. The second set of electronics 860-2 maybe arranged at or adjacent to the proximal end portion 819 of the scope 814. In implementations, the second set of electronics 860-2 is omitted such that substantially all electronics of the hub assembly 812 are arranged in a distal half of the imaging rod 814. The electronics 860-1 may include a light source such as a LED, which may be positioned adjacent to and proximal of the imaging sensor 808.

The center of mass CM may be established at a longitudinal position between the distal and proximal end portions 815, 819 of the hub assembly 812, including within the scope 814. The center of mass CM may be established at a distance $L_{CM}$ cm from a proximal boundary of a first length L1 of the scope 814. The hub assembly 812 may be configured such that the center of mass CM is established according to any of the ratios of the distance $L_{CM}$ and first length L1 disclosed herein. In implementations, the hub assembly 812 may be configured such that the distance $L_{CM}$ is greater than or equal to 25 percent of the first length L1, more narrowly greater than or equal to approximately 50 percent of the first length L1, or even more narrowly greater than or equal to approximately 75 percent of the first length L1. In implementations, the distance $L_{CM}$ may be less than or equal to approximately 90 percent of the first length L1.

Arranging at least some, a majority of, or all electronics 860 and/or other internal components of the hub assembly 812 adjacent to the distal end portion 815 of the instrument 810 may be utilized to shift the center of mass CM of the hub assembly 812 relatively more distally relative to the proximal end portion 819 of the hub assembly 812, which may improve retention of the instrument 810 without intervention by the surgeon or assistant.

Figure 14:
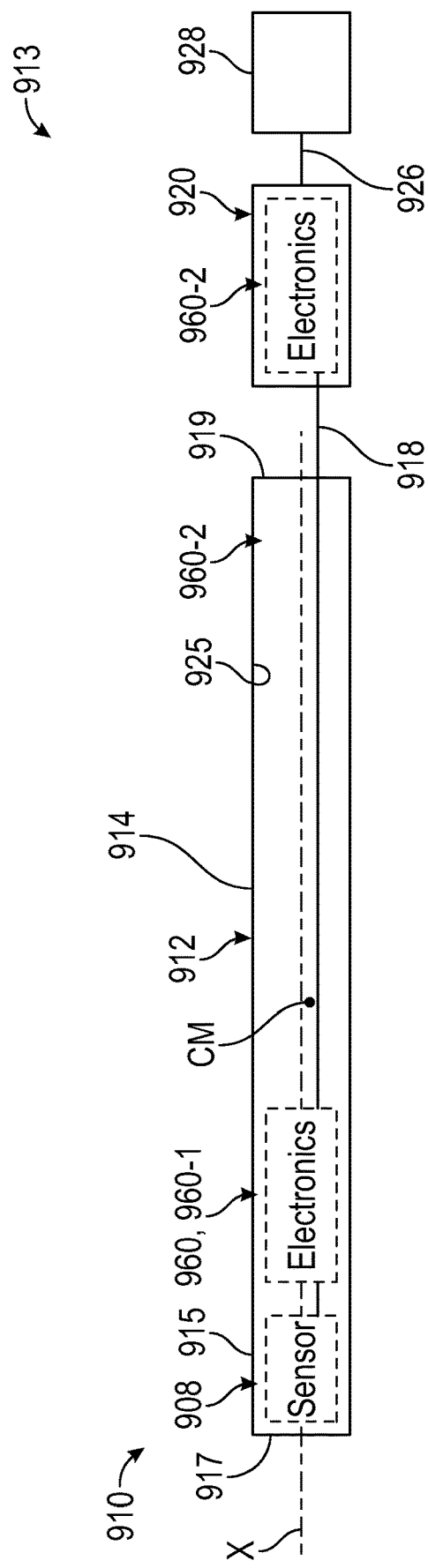
FIG. 14 illustrates another exemplary instrument.

Referring to FIG. 14, instrument 910 may include electronics 960. One or more of the electronics 960 may be incorporated into a cable assembly 913. The cable assembly 913 may include a button yoke 920, which may incorporate electronics 960-2. The electronics 960-2 can include any of the electronics disclosed herein, including the power supply 133, flexible circuit board 135, optical coupler 136, light supply 137 and/or electronic circuit 138 (FIG. 3). A separate hub including an enclosure to enclose the electronics may be omitted. The instrument 910 may include electronics 960-1 adjacent to a distal end portion 915 of an imaging rod 914, or the electronics 960-1 may be omitted and/or incorporated into the button yoke 920.

The novel devices and methods of this disclosure provide versatility in obtaining images of patient anatomy during an endoscopy. The disclosed instruments may be configured to allow the instrument to be inserted into the patient and to remain in position without being held or otherwise supported by a surgeon or assistant. The disclosed instruments may be configured to have a center of mass that improves retention of the instrument without intervention from the surgeon or assistant, which can decrease complexity and time to perform a surgical procedure.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. An endoscope for producing images of a surgery in vivo, the endoscope comprising:
   a hub;
   an imaging rod extending from the hub, the imaging rod being configured to receive light and direct the light to an area adjacent to a distal end portion of the imaging rod, wherein an imaging sensor is located at the distal end portion of the imaging rod, and the hub and the imaging rod are attached to form a hub assembly having a center of mass within the imaging rod; and
   wherein the imaging rod extends a first length between the distal end portion and an interface between the imaging rod and the hub, the center of mass is established within the imaging rod at a second length from the interface, and the second length is greater than or equal to 10 percent of the first length.

2. The endoscope of claim 1, wherein the hub comprises electronics configured to transmit image data from the imaging sensor.

3. The endoscope of claim 2, wherein the second length is greater than or equal to 25 percent of the first length.

4. The endoscope of claim 1, wherein the hub comprises a light supply.

5. The endoscope of claim 1, wherein the hub comprises a power supply.

6. The endoscope of claim 1, wherein the hub comprises electronics configured to transmit image data wirelessly.

7. The endoscope of claim 1, wherein the hub comprises electronics configured to transmit image data digitally.

8. The endoscope of claim 1, wherein the hub comprises electronics configured to transmit image data across a coaxial cable in an analog signal.

9. The endoscope of claim 1, wherein the hub assembly is symmetric with respect to a reference plane extending along a longitudinal axis of the hub assembly.

10. The endoscope of claim 1, wherein the hub is cylindrical.

11. The endoscope of claim 1, wherein the hub comprises:
    electronics including an electronic circuit, a light supply and an optical coupler;
    wherein the electronic circuit is configured to transmit image data from the imaging sensor;
    wherein the light supply is connected to the electronic circuit, and the light supply is configured to generate illumination in vivo;
    wherein the optical coupler is configured to communicate light from the light supply to a fiber optic, and the fiber optic is configured to transmit light from the hub to the distal end portion of the imaging rod;
    an enclosure configured to enclose the electronic circuit, the light supply and the optical coupler; and
    a hub coupler connecting the imaging rod to the enclosure.

12. The endo scope of claim 11, further comprising:
    a cable assembly including a first cable, a second cable, a connector and a button yoke having one or more controls; and
    wherein the first cable is coupled to a proximal end portion of the hub assembly, the button yoke interconnects the first and second cables, the second cable interconnects the button yoke and the connector, and the connector has a terminal configured to interface with an external device.

13. The endoscope of claim 1, wherein the hub includes an enclosure configured to enclose electronics.

14. The endoscope of claim 13, wherein the electronics are coupled to the imaging sensor.

15. The endoscope of claim 13, wherein the electronics are arranged adjacent to the distal end portion of the imaging rod.

16. The endoscope of claim 1, wherein the hub comprises:
    electronics including an electronic circuit and a light supply;
    wherein the electronic circuit is configured to transmit image data from the imaging sensor; and wherein the light supply is connected to the electronic circuit, and the light supply is configured to generate illumination in vivo.

17. The endoscope of claim 16, wherein:

the electronics include an optical coupler, and the optical coupler is configured to communicate light from the light supply to a fiber optic, and the fiber optic is configured to transmit light from the hub to the distal end portion of the imaging rod.

18. The endoscope of claim 17, wherein the hub comprises:

an enclosure configured to enclose the electronic circuit, the light supply and the optical coupler.

* * * * *